US006953661B1

(12) United States Patent
Diefenbach et al.

(10) Patent No.: US 6,953,661 B1
(45) Date of Patent: Oct. 11, 2005

(54) METHOD OF PREVENTING TRANSPORT OF A NEUROTROPIC VIRUS AND IDENTIFYING AGENTS FOR ACHIEVING SAME

(75) Inventors: Russell John Diefenbach, Northmead (AU); Monica Miranda-Saksena, Baulkham Hills (AU); Eve Margaret Diefenbach, Northmead (AU); David James Holland, Auckland (NZ); Anthony Lawrence Cunningham, Cheltenham (AU); Mark Penfold, Westmead (AU); Patricia Joan Armati, Rose Bay (AU)

(73) Assignees: Westmead Hospital, New South Wales (AU); The University of Sydney, Sydney (AU)

( * ) Notice: Subject to any disclaimer, the term of this patent is extended or adjusted under 35 U.S.C. 154(b) by 0 days.

(21) Appl. No.: 10/031,492

(22) PCT Filed: Jul. 20, 2000

(86) PCT No.: PCT/AU00/00873

§ 371 (c)(1),
(2), (4) Date: Jun. 10, 2002

(87) PCT Pub. No.: WO01/05410

PCT Pub. Date: Jan. 25, 2001

(30) Foreign Application Priority Data

Jul. 20, 1999 (AU) .............................................. PQ1719

(51) Int. Cl.[7] ................................................. C12Q 1/68
(52) U.S. Cl. ............................. 435/6; 435/5; 435/235.1
(58) Field of Search ............................ 435/6, 5, 235.1; 424/231.1, 143.1, 159.1, 204.1

(56) References Cited

U.S. PATENT DOCUMENTS 6,326,402 B1 * 12/2001 Kun et al. ................... 514/557
6,346,410 B1 *  2/2002 Beraud et al. ........... 435/252.3
6,455,293 B1 *  9/2002 Beraud et al. .............. 435/196
6,492,158 B1 * 12/2002 Beraud et al. .............. 435/196

FOREIGN PATENT DOCUMENTS

WO     WO 00/18919     4/2000

OTHER PUBLICATIONS

Sodeik et al . The Journal of cell Biology, Mar. 1997, vol. 136, pp. 1007–1021.*
Roller et al . Journal of Virology, Jun. 1992, pp. 3624–3632.*
Diefenbach, R.J.; "Herpes Simplex Virus Tegument Portein US11 Interacts with Conventional Kinesin Heavy Chain"; Journal of Virology, vol. 70, No. 7; Apr. 2002, pp. 3282–3291.
Penfold, Mark. E.T., "Axonal transport of herpes simplex virions to epidermal cells . . . " Proc. Natl. Acad. Sci. USA, vol. 91, pp. 6529–6533 (1994).
Miranda–Saksena et al, "Anterograde Transport of Herpes Simplex . . . , " Journal of Virology, Feb. 2000, pp. 1827–1839.
Holland et al, "Anterograde Transport of Herpes Simplex . . . ," Journal of Virology, Oct. 1999, pp. 8503–8511.
Topp et al, "Centripetal Transport of Herpes . . . ," Neuroscience, vol. 71, No. 4, pp. 1133–1144 (1996).
Bearer et al, "Retrograde axonal transport of herpes . . . ," PNAS, vol. 97, No. 14, Jul. 5, 2000, p. 8146–8150.
Guo–Jie Ye et al, "The Herpes Simplex Virus 1 . . . ," Journal of Virology, Feb. 2000, pp. 1355–1363.

* cited by examiner

Primary Examiner—Ali R. Salimi
(74) Attorney, Agent, or Firm—Nixon & Vanderhye (57) ABSTRACT

A method of preventing transport of a Herpes simplex virus within a neuron, comprising preventing interaction between a structural tegument protein US11 of the virus and a motor protein, Kinesin in the neuron such that virus transport in the neuron is prevented. An antiviral composition is also provided, comprising a compound capable of preventing interaction between a structural tegument protein of a neurotropic virus and a neuron or cell.

6 Claims, 5 Drawing Sheets

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Amino acid

<400> SEQUENCE: 1

Met Gly Arg Leu Glu
1               5

<210> SEQ ID NO 2
<211> LENGTH: 8
<212> TYPE: PRT
<213> ORGANISM: Artificial Sequence
<220> FEATURE:
<223> OTHER INFORMATION: Amino acid

<400> SEQUENCE: 2

Leu Asp Ser Met Gly Arg Leu Glu
1               5

<210> SEQ ID NO 3
<211> LENGTH: 19
<212> TYPE: PRT
<213> ORGANISM: Artificial Sequence
<220> FEATURE:
<223> OTHER INFORMATION: Amino acid -continued

```
<400> SEQUENCE: 3

Met Glu Ala Pro Gly Ile Arg Asp Pro Arg Ser Ser Phe Pro Tyr Gln
1               5                   10                  15

Pro His Pro
```

METHOD OF PREVENTING TRANSPORT OF A NEUROTROPIC VIRUS AND IDENTIFYING AGENTS FOR ACHIEVING SAME

TECHNICAL FIELD

The present invention relates to viral infections, particularly cellular and tissue interactions during infection.

BACKGROUND ART

Little is known about the mechanisms of transport of neurotropic viruses, such as Herpes simplex virus (HSV), varicella-zoster virus and rabies, within neuroses. For these viruses, which replicate in the nucleus, anterograde transport from the cell body of dorsal root human ganglionic (DRG) neurons to the axon terminus occurs over long distances. In the case of HSV, there is increasing evidence for separate, fast anterograde axonal transport of viral nucleocapsids coated with tegument along microtubules (MTs) and of glycoproteins in axonal transport vesicles. An understanding of the mechanisms of transport of these viruses would be of benefit. Once this information is obtained, means to interrupt or prevent this transport would be a good candidate for antiviral therapy.

HSV consists of an outer lipid envelope containing glycoproteins which surrounds the tegument. The inner capsid encloses the viral DNA to form the nucleocapsid. Early work has shown that HSV retrograde axonal transport in rat neurons utilizes microtubules (K. Kristensson, E. Lycke, J. Sjostranid, *Acta Neuropathol*, 17, 44, 1971). Previously, the present inventors have used a two chamber system to examine the mechanism of anterograde transport of HSV from infected dorsal root ganglionic (DRG) neurones in the central chamber along axonal fascicles to epidermal explants in the outer chamber. The velocity of viral transport (0.6 $\mu$m/s) indicated a mechanism based on fast anterograde transport (M. E. Penfold. P. Armati. A. L. Cunningham, *Proc. Natl. Acad. Sci.* USA 91, 6529, 1994). Using freeze-substitution transmission immuno-electron microscopy (TIEM) the virus was shown to be transported as unenveloped nucleocapsids, coated with tegument, separately from glycoproteins which are transported in vesicles (D. J. Holland, M. Miranda-Saksena, R. A. Boadle, P. J. Armati, A. L. Cunningham, *J. Virol.* 73, 8476, 1999). These findings were supported by experiments with nocodazole, an inhibitor of microtubule polymerization, and brefeldin A which inhibits transport through the Golgi. The transport of all three viral components, nucleocapsid, tegument and glycoproteins was inhibited by nocodazole, indicated their dependence on microtubule-associated transport. Brefeldin A, however, inhibited glycoprotein transport but not nucleocapsids confirming that the two are transported along separate pathways and indicating the close association of HSV glycoproteins with Golgi/intermediate compartment membranes.

The present inventors have now obtained useful evidence for the direct interaction between a viral structural tegument protein and an ubiquitous cellular protein. This new information has been used to develop methods and compositions to alter viral transport and movement in cells.

DISCLOSURE OF INVENTION

In a first aspect, the present invention provides a method of preventing or reducing transport of a neurotropic virus within a neuron or cell, the method comprising providing to said neuron or cell a compound preventing binding between a structural tegument protein of the virus and a motor protein in the neuron or cell such that virus transport in the neuron is prevented or reduced.

In a preferred embodiment, the neurotropic virus is Herpes simplex virus (HSV), varicella-zoster virus, or rabies virus. More preferably, the virus is HSV, the structural tegument protein is US11, and the motor protein is kinesin.

The method according to the invention can be carried out by providing a compound to a neuron or cell capable of preventing binding between a structural tegument protein of a neurotropic virus and a motor protein in a neuron or cell.

In one preferred form, the compound is a motor protein-like molecule which binds the structural tegument protein thereby preventing the normal interaction of the virus with cellular motor protein.

The motor protein-like molecule can be any suitable molecule and would include mimics of the motor protein or a parts of the motor protein to which the structural tegument protein binds.

When the motor protein is kinesin in the case of HSV, the kinesin-like molecule can be any suitable molecule and would include mimics of kinesin or a parts of kinesin to which the structural tegument protein US11 of HSV binds.

In another preferred form, the compound is a structural tegument-like molecule which binds to a motor protein of a neuron or cell thereby preventing the normal interaction between the neuron or cell with the virus. The structural tegument-like molecule can be a mimic of a viral tegument protein or a part of the tegument protein to which a cellular motor protein binds. Preferably, the virus is Herpes simplex virus, the structural tegument protein is US11, motor protein is kinesin and the structural tegument-like molecule is a mimic of US11 or a part of US11 to which the motor protein kinesin binds.

Knowing how these types of viruses move in neurons to infect neurons other cells and ultimately form lesions is an important advance and is useful for the development of antiviral strategies. Usually, during the latent state these viruses do not cause any real problems to an individual. It is during the active phase of the virus where clinical manifestations occur and suffering is caused. Preventing the actual transport of the virus down infected neurons should at least combat or prevent the clinical symptoms of re-infection. Similarly, preventing movement up the neuron may prevent the formation of latent state of the virus in ganglia or at least reduce the incidence of re-occurrence of manifestations of the disease in infected individuals.

In a second aspect, the present invention provides a modified neurotropic virus which has lost or has reduced ability to be transported in neurons, the virus comprising a mutation in a tegument protein such that the mutated tegument protein has abnormal interaction with a cellular motor protein.

In a third aspect, the present invention provides use of a compound to prevent or reduce the interaction between a neurotropic viral tegument protein with a cellular motor protein to prevent or reduce viral transport in a neuron.

In a preferred embodiment of the second and third aspects of the present invention, the neurotropic virus is Herpes simplex virus (HSV), varicella-zoster virus, or rabies virus. More preferably, the virus is HSV, the structural tegument protein is US11, and the motor protein is kinesin.

In a fourth aspect, the present invention provides an antiviral composition comprising a compound capable of preventing binding between a structural tegument protein of a neurotropic virus and a motor protein in a neuron.

Preferably, the neurotropic virus is selected from the group consisting of Herpes simplex virus, varicella-zoster virus, and rabies virus.

Preferably, the virus is Herpes simplex virus, the structural tegument protein is US11, and the motor protein is kinesin.

In one preferred form, the compound is a motor protein-like molecule which binds to the structural tegument protein of the virus thereby preventing normal interaction of the virus with cellular motor protein of a neuron. Preferably, the motor protein-like molecule comprises a mimic of a cellular motor protein or a part of the motor pain to which a so tegument protein of a virus binds.

In a further preferred form, the virus is Herpes simplex virus, the motor protein is kinesin a the motor protein-like molecule is a mimic of kinesin or a part of kinesin to which the structural tegument protein US11 of Herpes simplex virus binds.

In another preferred form, the compound is a structural tegument-like molecule which binds to a motor protein of a neuron or cell thereby preventing the normal interaction between the neuron or cell with the virus. The structural tegument-like molecule can be a mimic of a viral tegument protein or a part of the tegument protein to which a cellular motor protein binds. Preferably, the virus is Herpes simplex virus, the structural tegument protein is US11, motor protein is kinesin and the structural tegument-like molecule is a mimic of US11 or a part of US11 to which the motor protein kinesin binds.

The composition can further include additives, diluents, excipients and the like which can be used in clinical and health situations.

This study raises many questions about the mechanisms of tegument formation, location of US11 in the tegument of HSV, the potential role of motor proteins other than kinesin(s) and homologous interactions mediating the transport of other neurotropic viruses. Studies to map binding regions of US11 and uKHC and identification of other cellular factors which facilitate or contribute to the interaction will be useful. Inhibition of this interaction by peptides and/or peptidomimetic analogues could provide a new strategy for antiviral treatment for this and other neurotropic viruses. Incorporation of deletions into specifically attenuated live HSV (or other attenuated live neurotropic viruses) vaccine candidates could also be useful to prevent clinical recrudescence.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and drawings.

BRIEF DESCRIPTION OF DRAWINGS

FIG. 1. Transmission immuno-electron micrographs of human fetal axons labelled with 5 and 10 nm immunogold particles recognising HSV major capsid protein VP5 and the stalk of human uKHC respectively. Arrows =5 nm gold particles. Arrowheads=10 nm gold particles. Bars =200 nm (A and C) or 100 nm (B).

A Clustering of immunogold label for uKHC around axonal vesicles and diffuse labelling of other axons. Labelling with preimmune sera produced only sparse background label.

B Colocalization of the two immunogold labels against uKHC and VP5 over a dense unenveloped viral particle in an axon. Arrows=VP5 (5 nm gold particle).

C Extracellullar virus labelled only with anti-VP5. In the upper right corner is an axon with diffuse 10 nm immunolabel against uKHC. There is no immunolabel for uKHC over extracellular virus with only sparse background label outside axons.

FIG. 2. Identification of kinesin-binding HSV1 proteins. Mock or virus-infected Hep-2 cell lysates were incubated, as indicated (+), with His-KHC fragments bound to nickel-activated beads. Eluted kinesin-viral protein complexes were analysed by immunoblotting with appropriate antibodies.

A Polyclonal antibody to HSV1 identified major viral bands at 65 and 20 kDa bound preferentially to His-KHCstalk/tail.

B–C The viral proteins were identified with monoclonal antibodies as VP16 (B) and US11 (C), respectively. In each inmmunoblot, the first two lanes are controls for antibody specificity.

FIG. 3. Direct binding of US11 to uKHC and VP16. Shown are immunoblots of protein complexes eluted from nickel-activated beads.

A Lysates of bacteria expressing untagged KLC or US11 were incubated, as indicated (+), with His-KHC fragments. US11 bound only to His-KHCstalk/tail in the absence of other HSV1 proteins (lane 2, bottom panel). Overnight preincubation of the His-KHC fragments with KLC, which binds only to His-KHCstalk/tail (lane 4, top panel), prior to addition of US11, also showed binding of US11 but this was slightly reduced (lane 4, bottom panel).

B In a similar experiment, recombinant untagged VP16 did not bind to either His-KHC fragment (lanes 2 and 3). Expression of VP16 in bacterial lysates was confirmed in lane 1. Native VP16 from HSV1-infected Hep-2 cells (lanes 4 and 5) or recombinant untagged VP16 (lanes 6 and 7) was incubated with His-US11 or His-KHCstalk. Both forms of VP16 interacted with His-US11.

FIG. 4. Transport of structural HSV antigens into axons of infected dissociated rat neonatal neurons in vitro. Dissociated DRG neurons were infected with either wt HSV1 (CW strain), a US11 deletion mutant of HSV1 (R6604) or a US11 rescuant of R6604 (R6606) at 20 pfu/neuron. The appearance and transport into the principle axon of HSV1 tegument (US11), nucleocapsid (VP5) and envelope glycoprotein (gC) antigens was followed by serial fixation over 6 to 36 h, and then immunofluorescence and confocal microscopy. (A-I) HSV1 antigens in the axon at 24 h post infection (hpi). Bars=10 $\mu$m (A and C) or 25 $\mu$m (B and D-I). US11 was present in axons infected with wt HSV1 (A) but was completely absent from neurons infected with R6604 (B). US11 was expressed in neurons and present in axons infected with R6606 (C). VP5 was present in axons infected with wt HSV1

(D) but was not detected in axons infected with R6604 (E). VP5 was present in axons infected with R6606 (F). gC was detected in axons whether infected with wt HSV1 (G), R6604 (H) or R6606 (I).

FIG. 5. Ultrastructural distribution of enveloped and unenveloped nucleocapsids from an HSV1 US11 deletion mutant (R6604) in dissociated rat DRG neurons (26 hpi).

A Unenveloped (arrow) and enveloped (arrow head) nucleocapsids adjacent to the Golgi (G) within the cytoplasm of the cell body.

B Enveloped virions (arrow) in the extracellular space adjacent to the cell body and longitudinal section of an axonal process (arrowhead) containing microtubules.

MODES FOR CARRYING OUT THE INVENTION

METHODS

Antibody

HisKHC555-772, a oligohistidine (His)-tagged fragment of human. uKHC (R. J. Diefenbach, J. P. Mackay, P. J. Armati, A. L. Cunningham, *Biochemistry* 37, 16663, 1998), was used to generate chicken polyclonal anti-uKHC. The cell pellet from a 1 litre bacterial culture expressing HisKHC555-772 was resuspended in 25 ml of column running buffer (20 mM sodium diphosphate, pH 7.4. 0.5 M NaCl), lysed by sonication, clarified by centrifugation, and applied to a POROS 20 MC column (Perseptive Biosystems; 4.6×10 mm) which had been charged with nickel according to the manufacturer's instructions. The His-tagged fusion protein was eluted at 5 ml/min with 15 column volumes of a gradient from 0 to 0.5 M imidazole in running buffer. Pooled fractions containing purified HisKHC555-772 were then dialysed against PBS. Protein concentrations were determined using a Bio-Rad protein assay. A total of 2 mg of protein was then used to raise a polyclonal antibody in chickens (a service provided by the Institute of Medical and Veterinary Science. Veterinary Services Division, Gilles Plains, South Australia). Pre- and post-immune serum from a single immunised chicken was subsequently used in this study. The antibody was shown to be specific in immunoblots for human uKHC by comparing reactivity with the immunising antigen against human neuronal (n) KHC (expressed as a His-tagged fragment spanning amino acids 409-1032). cDNAs for uKHC (F. Navone, et al., *J. Cell Biol.* 117, 1263, 1992) and nKHC (J. Niclas, F. Navone, N. Hom-Booher. R. D. Vale, *Neuron* 12, 1059, 1994)) were provided by R. Vale.

HisKHC Proteins

The HisKHC proteins were expressed, harvested, bound to, and eluted from nickel-activated beads as previously described (R. J. Diefenbach, J. P. Mackay, P. J. Armati, A. L. Cunningham, *Biochemistry* 37, 16663, 1998). Generation of virus stocks and titrations of wt HSV1 (CW1) and modified viruses were performed in Hep-2. For binding assays, Hep-2 cells were infected at a multiplicity of 5 pfu/cell and incubated for 24 h. Cell monolayers were washed twice with PBS, resuspended in PBS (1×10$^6$ cells/ml), freeze-thawed 3 times, sonicated for 15 s, before addition of 1% (v/v) NP-40 and incubation for 1 h at 4° C. The soluble fraction was harvested by centrifugation at 4° C. (10000g for 15 min) before addition (1 ml) to HisKHC fragments on nickel-activated beads. Beads were incubated overnight with rocking at 4° C. washed with ×20 volumes of wash buffer (150 mM NaCl, 120 mM imidazole, 20 mM Tris-HCl , pH 7.9), prior to elution of bound protein complexes. Protein complexes were separated by SDS-PAGE and identified by immunoblotting as previously described (R. J. Diefenbach, J. P. Mackay, P. J. Armati, A. L. Cunningham, *Biochemistry* 37, 16663, 1998). Antibodies used included mouse monoclonal anti-US11 (R. J. Roller, B. Roizman, *J. Virol.* 66, 3624, 1992) (provided by B. Roizman), mouse monoclonal anti-VP16 (C. McLean. et al., *J. Gen. Virol.* 63, 297, (1982) (LP1; provided by T. Minson) and rabbit polyclonal anti-HSV1 from Dako. Rabbit polyclonal antibody to HSV1 capsid protein VP5 was provided by G. Cohen and R. Eisenberg (G. H. Cohen, et al., *J. Virol.* 34, 521, 1980). Mouse monoclonal antibody to HSV1 gC and KLC (L2) was obtained from Chemicon International.

Plasmids

Plasmid pRB4766 (H. Tsiang, E. Lycke, P. E. Ceccaldi, A. Ermine, X. Hirardot, *J. Gen. Virol* 70, 2075, 1989) containing HSV1 US11 genomic DNA in pGEX-KG was provided by B. Roizman. An untagged US11 construct was generated by digestion of pRB4766 with NcoI and insertion into the NcoI site of pET-28a. This resulted in an additional five amino acids (MGRLE-SEQ ID NO:1) at the N-terminus of US11. His-tagged US11 was constructed by inserting an EcoRl/Fspl US11-containing fragment from pRB4766 into EcoRl/Hindlll (Klenow filled-in) digested pET-28c. Between the oligohistidine tag and US11 sequence are inserted amino acids LDSMGRLE (SEQ ID NO:2). Genomic DNA containing HSV1 VP16 was provided by P. O'Hare (T. A. Hughes, S. LaBoissiere, P. O'Hare, *J. Biol. Chem.* 274, 16437, 1999; D. O'Reilly, O. Hanscombe, P. O'Hare, EMBO J. 16, 2420, 1997). The plasmid pPO54 consisted of the gene for VP16 inserted into the BamHI site of pBS. An untagged VP16 construct was generated by firstly digesting pPO54 with BamHl and inserting into the BamHl site of pET-28c. VP16 was subsequently released from pET-28c by digestion with BamHl/Xhol and inserted into the yeast vector pACT2 also cut with BamHl/Xhol. VP16 was then released with an Ncol/Xhol digest and reinserted into the Ncol/Xhol site of pET-28a to allow expression of untagged VP16. The resulting fusion protein had an additional nineteen amino acids (MEAPGIRDPRSSFPYQPHP-SEQ ID NO:3) at the N-terminus of VP16. Bacteria expressing untagged US11, VP16 or KLC (R. J. Diefenbach, J. P. Mackay, J. Armati, A. L. Cunningham, *Biochemistry* 37, 16663, 1998) were lysed in normal salt binding buffer (150 mM NaCl, 5 mM imidazole, 20 mM Tris-HC1.pH 7.9) for use in bonding assays as described above.

Virus Mutants

R6604 is a partial US11 gene deletion mutant which does not express the US11 protein and R6606 is US11 rescuant of R6604. To generate the HSV1 mutant R6604 (US11-), a plasmid carrying a deletion in the US11 coding sequence was constructed (pRB5173) by deleting the sequences present between BspEI and XhoI in the BamHI Z fragment of HSV1(F) genome. The 132 nucleotides deleted from the fragment removed all three ATG codons of the US11 ORF without affecting the adjacent US12 ORF. The plasmid was cotransfected with the R3630 recombinant virus DNA containing the thymidine kinase gene inserted into US12. The selected recombinant progeny (R6603) contained a US11 gene lacking the 132 nucleotides but an intact US12. The thymidine kinase gene at its natural locus was then restored to yield R6604. The genotype and phenotype of all recombinants was verified by Southern analysis and immunoreactivity of its proteins.

RESULTS

The candidate motor proteins for viral transport should be those involved in microtubule-dependent fast axonal antero-grade transport of organelles, most likely the conventional kinesins (ubiquitous and neuronal) or possibly the kinesin-related protein KIF3. The colocalization of kinesin and HSV1 nucleocapsids was examined in fetal human neurons using the DRG neuron-epidermal explant two chamber model system as previously described (D. J. Holland, M. Miranda-Saksena, R. A. Boadle, P. J. Armati, A. L. Cunningham, *J. Virol.* 73, 8476, 1999). Anterograde axonal transport of HSV1 (CW strain; D. J. Holland, M. Miranda-Saksena, R. A. Boadle, P. J. Armati, A. L Cunningham, *J. Virol.* 73, 8476, 1999) was visualized using freezesubstitution TIEM. Dual immunogold labelling (5 and 10 nm gold particles) of axons was performed with chicken polyclonal antibody to ubiquitous kinesin heavy chain (uKHC) and rabbit polyclonal antibody to HSV1 major capsid protein VP5 (G. H. Cohen, et al., *J. Virol.* 34, 521, 1980).

Figure 1A:
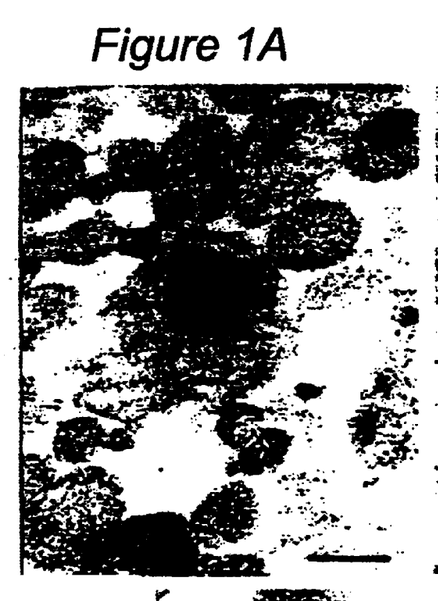
Figure 1B:
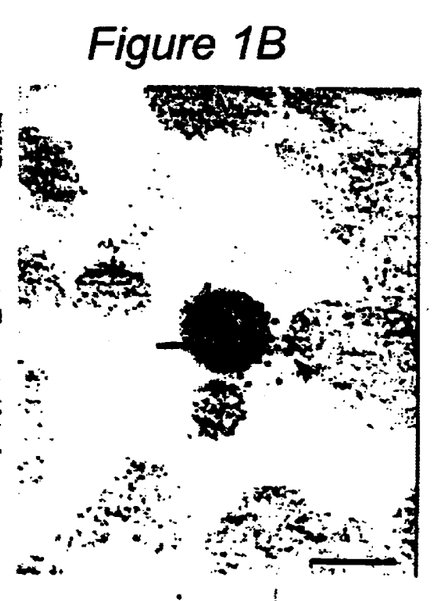
Figure 1C:
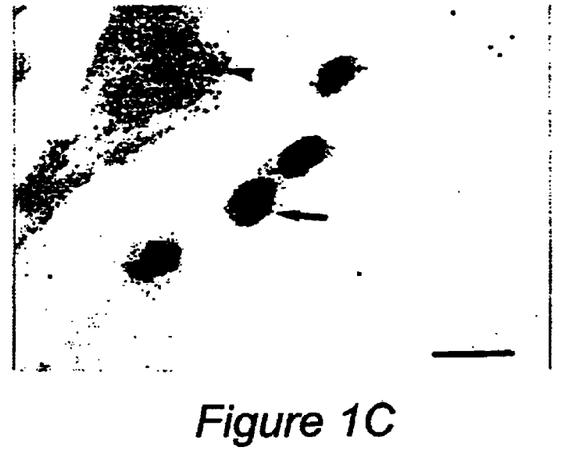

Anti-uKHC showed diffuse labelling throughout axons with clusters of immunolabel for uKHC observed around electron dense axonal vesicles (FIG. 1A). Only sparse background label was found extra-axonally. With pre-immune sera only sparse background immunolabel was present on sections and there was no labelling of axonal vesicles. Immunolabel for uKHC and VP5 was found in and around unenveloped HSV1 nucleocapsids, respectively, within axons (FIG. 1B). The anti-VP5 antibody was specific with no labelling of axons in mock-infected cultures. Only VP5 and not kinesin immunolabel was present on extracellular virus (FIG. 1C). The immunolabelling for uKHC over intra-axonal virus (but not extra-axonal virus) was as intense as that around axonal vesicles and provides strong direct evidence that kinesin is involved in the anterograde axonal transport of HSV. The tegument protein VP16 has been demonstrated to colocalize with VP5-labelled nucleocapsids during anterograde transport (D. J. Holland, M. Miranda-Saksena, R. A. Boadle, P. J. Armati, A. L. Cunningham, *J. Virol.* 73, 8476, 1999). Therefore, tegument or outer capsid proteins are candidates for binding to conventional ubiquitous kinesin.

Conventional kinesin is a heterotetramer consisting of two identical heavy and two identical light chains. The heavy chain has a three domain structure consisting of a N-terminal motor domain, highly conserved among the kinesin superfamily, a central stalk domain containing heptad repeats and a C-terminal tail domain. The present inventors used fragments of human uKHC tagged at the N-terminus with an oligohistidine (His) sequence, which were generated and characterised previously, as bait to identify kinesin-binding HSV1 proteins. In this work the fragments were designated His-KHCstalk (amino acid residues 555-772) and His-KHCstalk/tail (residues 771-963).

Figure 2A:
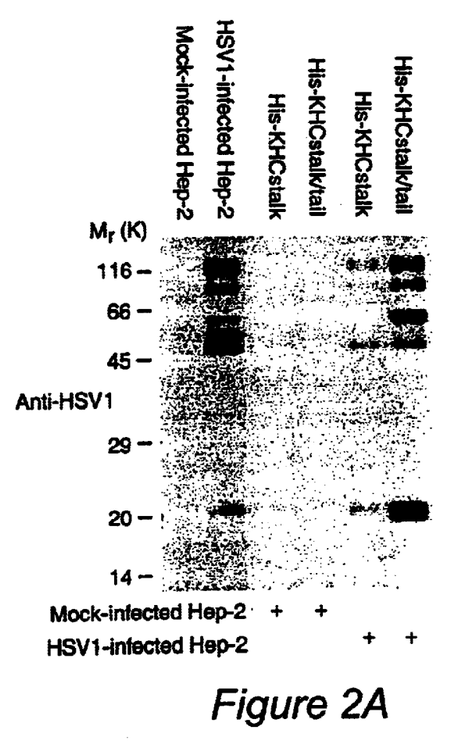
Figure 2B:
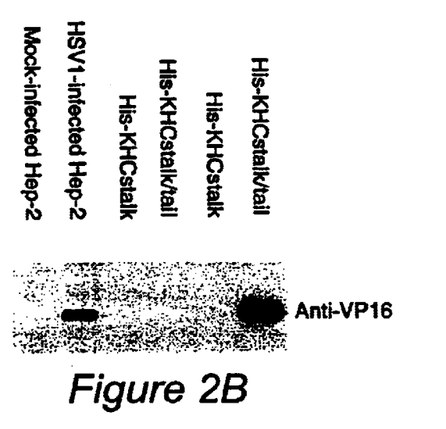
Figure 2C:
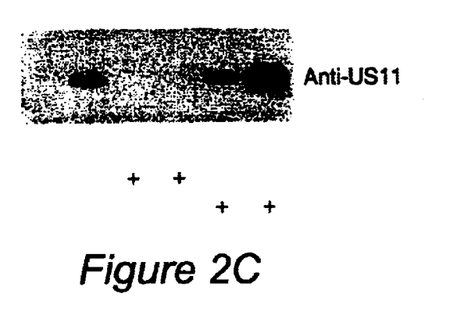

HisKHC fragments attached to nickel-activated beads were incubated with a lysate of mock or HSV1-infected Hep-2 cells. Analysis of eluted complexes by immunoblotting with anti-HSV1 identified predominantly a 65 and 20 kDa viral protein preferentially bound to KHCstalk/tail (FIG. 2A). These viral proteins were subsequently identified as the tegument proteins VP16 (FIG. 2B) and US11 (FIG. 2C).

Figure 3A:
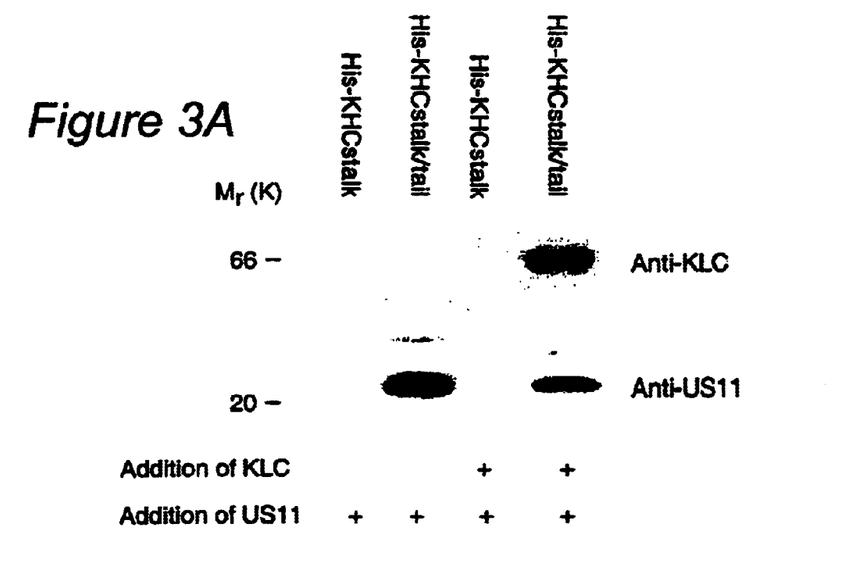

To establish whether US11 and/or VP16 bound directly to uKHC, untagged forms of both were expressed in *Escherichia coli*. Addition of untagged US11 to HisKHC showed that US11 binds specifically to KHCstalk/tail (FIG. 3A. bottom panel). This also showed that the binding of US11 to uKHC can occur in the absence of other viral proteins although it may well be modulated in vivo by viral or cellular factors. A complex of uKHC and KLC was generated by preincubating HisKHCstalk/tail with untagged KLC (FIG. 3A, top panel). This kinesin heavy/light chain complex also binds US11, though at a slightly reduced level when compared with heavy chain alone (FIG. 3A, bottom panel lanes 2 and 4). The minor reduction in US11 binding is probably due to steric effects and not competitive inhibition since KLC and US11 bind to different regions of HisKHCstalk/tail. Therefore, KLC appears not to be directly involved in binding US11 as there was no increase in the level of US11 bound to a heavy/light chain complex compared with heavy chain alone. A similar observation has been documented using a KHCstalk/tail fragment from sea urchin which can bind to vesicles in the absence of KLC.

Figure 3B:
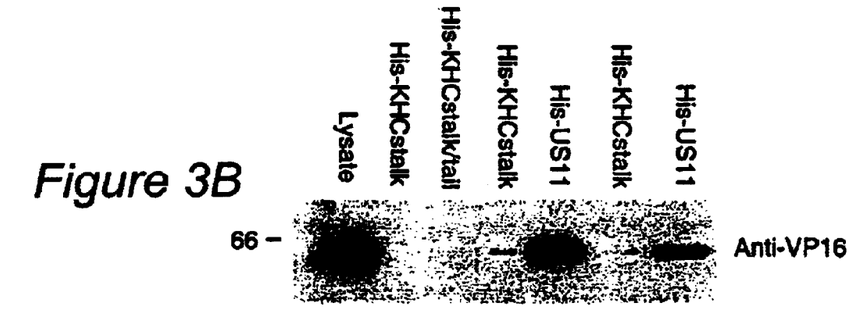

In contrast, VP16 does not bind directly to uKHC (FIG. 3B). The presence of VP16 co-eluting with KHC after incubation with viral lysates can be explained by the observation that VP16 binds directly to US11 (FIG. 3C). This binding was observed with both native and recombinant VP16 (in the absence of other viral proteins). Therefore uKHC binds US11 which in turn binds VP16. This VP16/US11 interaction may represent an important structural interaction for US11 in the tegument of the virus or may play a regulatory role in infected cells. VP16 has also been shown to bind to other tegument proteins including vhs (C. A. Smibert, B. Popova, P. Xiao, J. P. Capone, J. R. Smiley, *J. Virol.* 68. 2339, 1994) and VP22 (G. Elliott, G. Mouzakitis, P. O'Hare, *J. Virol.* 69, 7932, 1995), as well as to glycoprotein (gD; Q. Zhu, R. J. Courtney, *Virology* 204, 590, 1994). Therefore US11, a structural viral protein proposed to be part of the tegument, may also interact with one or both of these other tegument proteins.

US11 appears to be a multi-functional protein. It is a basic phosphoprotein which has RNA-binding activity, stably associates with 60S ribosomal subunits, has a role in post-transcriptional regulation of gene expression and localizes to the nucleoli. The RNA-binding properties of US11 are dependent on the 20–24 RXP-repeats in the carboxy-half of the protein while the amino-half of US11 is required for transactivation of gene expression. It has been suggested that the N-terminal domain may be involved in transport and translation of mRNA from the nucleus to the cytoplasm. This amino domain may well also bind to kinesin. The US11 protein is well conserved between HSV1 and 2 (63% homology) with the greater variation at the N-terminus. There are no US11 homologues in varicella-zoster virus or rabies suggesting this virus may use different proteins for anterograde axonal transport. However, there are precedents though within the herpesviruses for similar functions on different proteins (eg entry into cells via gD in HSV (J. Rajcani, A. Vojvodova, *Acta Virol.* 42, 103, 1998) and via gE/I and gB in varicella zoster virus C. Grose, *Rev. Infect. Dis.* Suppl. 11, S960, 1991).

To test the hypothesis that the US11-uKHC interaction mediated anterograde transport of HSV into the axons of rat neonatal DRG neurons, the axonal transport of wild-type (wt) HSV1, a US11 deletion mutant of HSV1 and its rescuant were examined. The appearance and distribution of structural HSV protein antigens from the tegument (US11), nucleocapsid (VP5) and envelope (gC) and their anterograde transport into axons of dissociated rat neonatal DRG was followed by fixation at serial time points over 24 hours and immunofluorescence/confocal microscopy.

Figure 4A:
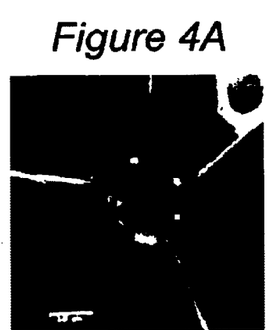
Figure 4B:
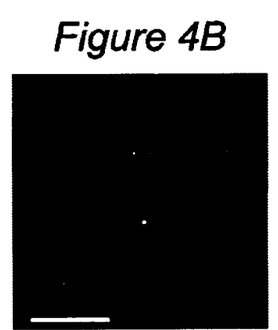
Figure 4C:
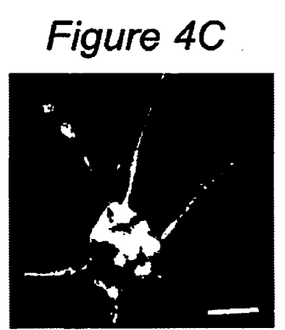
Figure 4D:
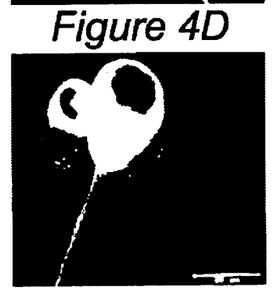
Figure 4E:
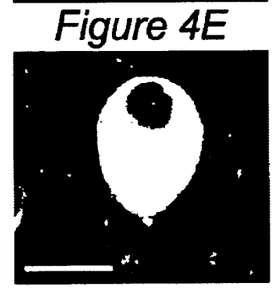
Figure 4F:
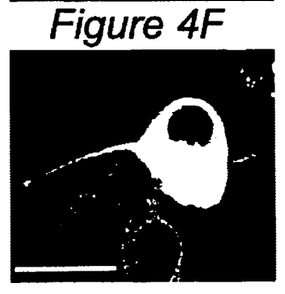
Figure 4G:
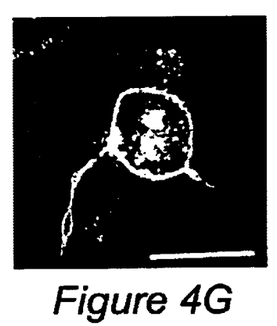
Figure 4H:
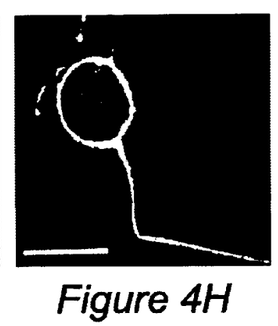
Figure 4I:
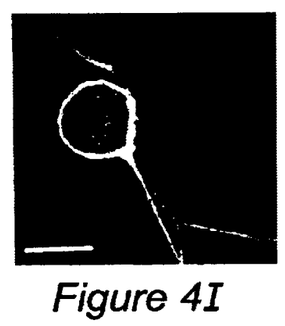
Figure 5:
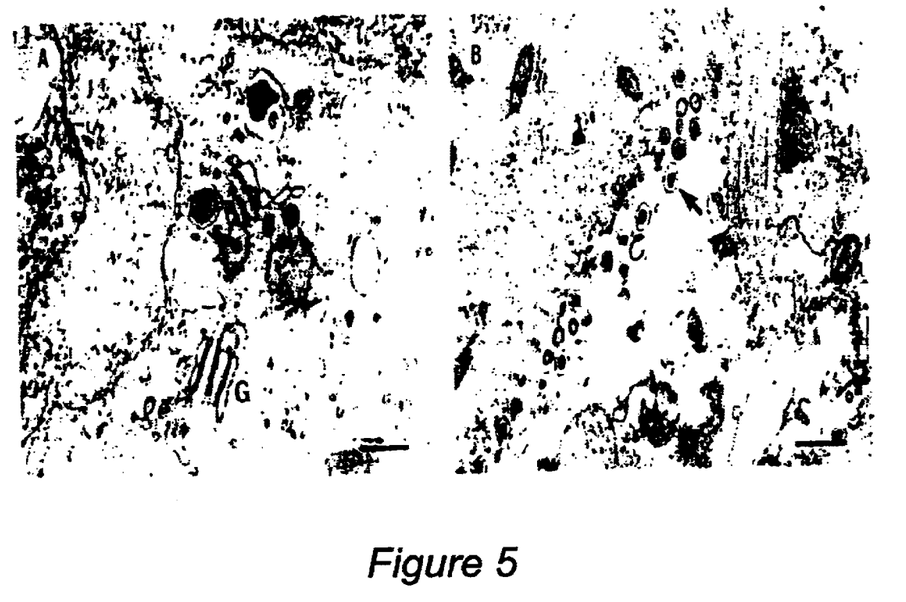

Firstly, US11 antigen from wt HSV1 (CW clinical strain), was demonstrated to move down the axon (a criterion for its proposed role in anterograde axonal transport: FIG. 4A). The protein was not expressed in the US11 deletion mutant of HSV1, R6604, but was present in the US11 rescuant of R6604, R6606 (FIGS. 4B and C). The kinetics of transport of US11 into axons was similar for wt and R6606 (FIG. 4A and C). In neurons infected with wt HSV1. VP5 antigen was diffusely distributed in the cytoplasm of the cell body and transported throughout the axon by 24 hours (FIG. 4D). The kinetics of transport of US11 and VP5 from wt HSV1 into axons was similar, supporting colocalization of US11 with nucleocapsids (FIGS. 4A and D). In contrast, deletion of US11 in R6604 abrogated nucleocapsid transport into axons since no VP5 antigen could be detected in the axons of infected neurons (FIG. 4E), although there was a similar diffuse cytoplasmic distribution of VP5 to wt HSV1 (FIGS. 4D and E). Rescue of US11 expression in R6606 restored HSV1 nucleocapsid transport into and along axons at a rate similar to wt (FIG. 4F). Anterograde transport of gC from either wt HSV1, R6604 or R6606 into axons was unaffected (FIG. 4G–I). For R6604, transmission electron microscopy at late time points (26 hours) showed large numbers of enveloped virions in the extracellular space and in the cytoplasm of the cell body of neurons, concentrated around the Golgi (FIGS. 5A and B). Unenveloped nucleocapsids were in variable abundance in the nuclei and sparsely scattered in the perinuclear cytoplasm, often adjacent to the Golgi (FIG. 5A). Thus the absence of US11 does not prevent transport across the nuclear membrane, normal envelopment and viral egress in the cell body. Thus, there is no observable functional disruption of the tegument.

These findings suggest that there are two separate mechanisms of viral egress, one via the cell body and the other via axon termini. The absence of US11 appears to disrupt the latter pathway between the cell body and the axon. The presence of US11 in the tegument, the similar kinetics of anterograde transport of US11 and nucleocapsid VP5, and the inability of a HSV mutant deleted in US11 to be transported into axons is consistent with the hypothesis that the observed US11-uKHC interaction has a major role in mediating anterograde transport of nucleocapsids into and along axons.

Knowing how these types of viruses move in neurons to infect neurons, other cells and ultimately form lesions is an important advance and is useful for the development of antiviral strategies. Usually, during the latent state these viruses do not cause any real problems to an individual. It is during the active phase of the virus where clinical manifestations occur and suffering is caused. Preventing the actual transport of the virus down infected neurons should at least combat or prevent the clinical symptoms of re-infection. Similarly, preventing movement up the neuron may prevent the formation of latent state of the virus in ganglia or at least reduce the incidence of re-occurrence of manifestations of the disease in infected individuals.

This work raises many possibilities about the mechanisms of tegument formation, location of US11 in the tegument of HSV, the potential role of motor proteins other than kinesin(s) and homologous interactions mediating the transport of other neurotropic viruses. Inhibition of this interaction by peptides and/or peptidomimetic analogues could provide a new strategy for antiviral treatment for this and other neurotropic viruses. Incorporation of deletions into specifically attenuated live HSV (or other attenuated live neurotropic viruses) vaccine candidates could also be useful to prevent clinical recrudescence.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of preventing transport of a Herpes Simplex virus within a neuron or cell, the method comprising providing to said neuron or cell a compound specifically preventing binding between the structural tegument protein, US11 of the virus and the motor protein, kinesin in the neuron or cell such that virus transport in the neuron or cell is prevented.

2. The method according to claim 1 wherein the compound is a mimic of kinesin or a part of Kinesin to which US11 binds.

3. The method according to claim 1 wherein the compound is a mimic of US11 or a part of US11 to which kinesin binds.

4. A method of screening for a compound that inhibits transport of a Herpes Simplex virus within a neuron or cell, the method comprising determining whether a compound to be screened prevents binding between the structural tegument protein, US11 of the virus and the motor protein, kinesin in the neuron or cell.

5. The method according to claim 4 wherein the compound is a mimic of kinesin or a part of kinesin to which US11 binds.

6. The method according to claim 4 wherein the compound is a mimic of US11 or a part of US11 to which kinesin binds.

* * * * *